United States Patent
Riedel

(10) Patent No.: US 10,043,363 B2
(45) Date of Patent: Aug. 7, 2018

(54) SYSTEM AND A METHOD FOR DETECTING LOW CONCENTRATIONS OF SPECIFIC CHEMICAL COMPOUNDS IN THE AIR OF AN AIRCRAFT CABIN

(71) Applicant: Airbus Operations GmbH, Hamburg (DE)

(72) Inventor: Christian Riedel, Hamburg (DE)

(73) Assignee: Airbus Operations GmbH, Hamburg (DE)

( * ) Notice: Subject to any disclaimer, the term of this patent is extended or adjusted under 35 U.S.C. 154(b) by 0 days.

(21) Appl. No.: 15/711,222

(22) Filed: Sep. 21, 2017

(65) Prior Publication Data

US 2018/0082558 A1    Mar. 22, 2018

(30) Foreign Application Priority Data

Sep. 22, 2016  (EP) .................................. 16190247

(51) Int. Cl.
G08B 21/00 (2006.01)
G08B 17/117 (2006.01)
G08B 21/16 (2006.01)
B64D 45/00 (2006.01)

(52) U.S. Cl.
CPC ............ *G08B 17/117* (2013.01); *B64D 45/00* (2013.01); *G08B 21/16* (2013.01); *B64D 2045/009* (2013.01)

(58) Field of Classification Search
CPC ......... C07C 51/09; C07C 67/10; C07C 53/08; C07C 69/24; C07C 51/353; C07C 67/343; B01J 2231/40; B01J 2531/821; B01J 31/2208

USPC .................................................. 340/945, 628
See application file for complete search history.

(56) References Cited

U.S. PATENT DOCUMENTS

| 7,824,479 | B2 | 11/2010 | Rowley et al. |
| 2006/0153740 | A1* | 7/2006 | Sultan ............ B60K 28/06 422/88 |
| 2008/0283663 | A1 | 11/2008 | Space et al. |

(Continued)

FOREIGN PATENT DOCUMENTS

| EP | 2 703 049 | 3/2014 |
| WO | WO 00/68675 | 11/2000 |

OTHER PUBLICATIONS

Extended Search Report for EP16190247.3 dated Mar. 24, 2017, 9 pages.

*Primary Examiner* — Ojiako Nwugo
(74) *Attorney, Agent, or Firm* — Nixon & Vanderhye P.C.

(57) ABSTRACT

A system for detecting low concentrations of specific chemical compounds in the air of an aircraft cabin. The system includes a cabin management system with a processing unit and a user interface and a plurality of sensors. Each sensor is connected to the processing unit of the cabin management system such that data can be transmitted from the sensor to the processing unit. Each sensor is adapted to determine a presence of a first chemical compound in the air of an aircraft cabin and transmit data indicative of the determined presence to the processing unit. The processing unit is adapted to process data indicative of the presence of the first chemical compound received from a sensor of the plurality of sensors and to signal the presence of the first chemical compound to a user via the user interface.

11 Claims, 2 Drawing Sheets

(56) References Cited

U.S. PATENT DOCUMENTS

| | | | |
|---|---|---|---|
| 2010/0277345 A1* | 11/2010 | Rodriguez | G01T 1/167 340/945 |
| 2012/0122075 A1* | 5/2012 | Call | B01D 45/04 435/3 |
| 2013/0030718 A1 | 1/2013 | Williams et al. | |
| 2013/0137183 A1* | 5/2013 | Nacson | G01N 30/00 436/92 |
| 2013/0197739 A1* | 8/2013 | Gallagher | B64F 5/60 701/31.5 |
| 2015/0302669 A1* | 10/2015 | Gonnsen | G01M 5/0075 701/23 |
| 2016/0093481 A1* | 3/2016 | Bick | H01J 49/0031 250/282 |
| 2016/0334547 A1* | 11/2016 | MacNeille | G01W 1/02 |

\* cited by examiner

SYSTEM AND A METHOD FOR DETECTING LOW CONCENTRATIONS OF SPECIFIC CHEMICAL COMPOUNDS IN THE AIR OF AN AIRCRAFT CABIN

RELATED APPLICATION

This application claims priority to European Patent Application 16190247.3 filed Sep. 22, 2016.

FIELD OF THE INVENTION

The present invention is directed to a system for detecting low concentrations of specific chemical compounds in the air of an aircraft cabin. The system comprises a cabin management system and a plurality of sensors. The cabin management system comprises a processing unit and a user interface. Each sensor of the plurality of sensors is connected to the processing unit of the cabin management system such that data can be transmitted from the sensor to the processing unit. The invention is further directed to an aircraft cabin comprising a system for detecting low concentrations of specific chemical compounds in the air of the aircraft cabin and a method for detecting low concentrations of specific chemical compounds in the air of an aircraft cabin.

BACKGROUND AND SUMMARY OF THE INVENTION

Safety onboard aircraft has been a growing concern in recent years. A particular risk factor on board an aircraft are passengers with doubtful intentions. Therefore, every passenger and every luggage item is searched at the airport for objects considered unsafe. In addition to the ongoing search for weapons or objects that could be used as a weapon, in recent years passengers and their luggage have also been frequently searched for chemical substances or compounds that could be used as explosives. The search for chemical substances is usually performed at airport security when passengers enter the gate area of the airport. A sample is taken from a passenger by wiping a probe across the passenger, the passenger's clothing and/or the passenger's luggage. The sample is then analyzed in a dedicated scanner for remnants of chemical substances that could be part of explosives.

The present invention may be embodied to provide an alternative means and an alternative method for detecting chemical compounds that could be used as explosive or to form explosives and to prevent that such chemical compounds can be used by a passenger with doubtful intentions onboard an aircraft.

In a first aspect the problem is solved by system for detecting low concentrations of specific chemical compounds in the air of an aircraft cabin as specified above, wherein each sensor of the plurality of sensors is adapted to determine a presence of a first chemical compound in the air of an aircraft cabin and transmit data indicative of the determined presence to the processing unit. The processing unit is adapted to process data indicative of the presence of the first chemical compound received from a sensor of the plurality of sensors and to signal a user via the user interface if data indicative of the presence of the first chemical compound has been processed by the processing unit.

In other words the system according to the present invention is provided for detecting low concentrations of selected chemical compounds or substances in the air that circulates through the cabin of an aircraft or into and out of the cabin of the aircraft. In the context of the present invention detecting a specific or selected chemical compound refers to detecting the presence of a chemical compound in the air and to be able to indicate which chemical compound or substance has been detected. This is in contrast to existing smoke detectors which are unspecific with regard to the material that is found in the air circulating through the cabin.

The system is based on an existing cabin management system which comprises amongst others a processing unit and a user interface. Such cabin management systems are widely used in civil aircraft. They are used, for example, to control the cabin lighting and the air conditioning. Further, the cabin management system may, for example, be connected to so-called passenger service units which are frequently installed above the seats in an aircraft. The passenger service units or PSUs can, for example, provide passengers with a reading light, individual ventilation and a button for calling a flight attendant. More advanced PSUs may also provide in-flight entertainment functions and/or oxygen supply in case of a loss in cabin pressure.

The cabin management system comprises a processing unit, for example, a server. The processing unit may be the central processing unit of the cabin management system which also provides additional features such as lighting and air-conditioning control. Such a central processing unit may also be referred to as the director of a cabin management system. However, it is also conceivable that an additional processing unit is provided for providing the functions required by the system according to the present invention. The processing unit may be a microprocessor.

The user interface of the cabin management system may, for example, be a display device in the form of a liquid crystal display with touch control. The user interface could, for example, be formed by the so-called flight attendant panel which provides flight attendants the means for controlling parameters of the cabin management system such as the temperature of the cabin and lighting of the cabin. However, the user interface could also be formed as a remote device such as a tablet. It is also conceivable that the user interface is formed by an array of lamps, e.g., light emitting diodes, which have been labeled such that they can signal the information required by the respective embodiments of the system.

The system further comprises a plurality of sensors. These sensors are connected to the processing unit of the cabin management system for transmitting data from the sensor to the processing unit. In other words, some kind of connection is provided between each sensor and the processing unit such that the data which needs to be transmitted in the system can be transmitted. Data can be transmitted in digital form. However, it is also conceivable that data is transmitted in form of an analog signal from the sensor to the processing unit. The connection between the sensors and the processing unit can, for example, be established using the existing data network of an aircraft cabin which is also used for connecting, for example, the central processing unit of the cabin management system to the PSUs. The data network may, for example, be an Ethernet network. However, it is also possible to use a wireless connection between the sensors and the processing unit or data distribution units of the data network of the aircraft cabin. The network may not only provide data transmission from the sensor to the central processing unit but also in the opposite direction.

Each of the sensors is adapted to determine a presence of a first chemical compound in the air of an aircraft cabin, i.e., the sensor can determine if the air in the aircraft cabin comprises particles of a specific first chemical compound. The chemical compound may, for example, be an explosive or another hazardous material such as an acid. Miniaturized detectors which are able to detect very low concentrations of airborne particulate chemical compounds or chemical compounds in the gas phase are known to the skilled person. They may, for example, be microfluidic devices employing spectroscopic principles. Such devices use, for example, miniaturized CCDs and may operate in the infrared or visible spectrum.

If one of the sensors determines that the first chemical compound is present in the air of the aircraft cabin, corresponding data is transmitted to the processing unit. The sensor may, for example, transmit a digital signal indicating that a first chemical compound was detected. However, it is also possible that the sensor transmits, for example, the raw sensor data and the sensor data is analyzed by the processing unit. For example, the sensor may transmit the result of a spectroscopic analysis of the cabin air to the processing unit. In that case, data would also be transmitted when no presence of a first chemical compound has been detected in the air of the aircraft cabin. However, as long as no presence of a chemical compound has been detected in the air of the aircraft cabin, the data is not indicating a presence of a chemical compound and no data indicative of the presence of a chemical compound is processed by the processing unit.

The processing unit is adapted to process the data received from and transmitted by the sensor which data is indicative of the presence of the first chemical compound. Processing may, for example, involve analyzing received spectroscopic data. However, in other embodiments processing the received data could also mean that the content of the received data is extracted from a received data packet and relayed to the user interface.

The processing unit is further adapted to control the user interface. In particular, the processing unit uses the user interface to signal a user if the data indicating the presence of the first chemical compound has been processed by processing units. In other words, the processing unit warns a user if the first chemical compound was detected by one of the sensor. Signaling may, for example, be done by displaying a message on a display or by lighting an indicator light provided to this end. In an exemplary preferred embodiment signaling does not only include a mere signaling that some kind of a first chemical substance has been detected but also which first chemical substance and by which of the plurality of sensors.

The system according to the present invention advantageously allows the detection of chemical compounds that may be used as explosives not only at the airport security but also inside an aircraft cabin. This may provide additional safety compared to safety provided by airport security control. A particular advantage of a system located in an aircraft cabin is that such a system cannot be skipped and it may also detect explosive chemical compounds that have been manufactured from harmless chemical compounds after security on the airport has been successfully passed. A further advantage of the system according to the present invention is that it uses the existing structure of the cabin management system which may already provide the necessary data network, the processing unit and the user interface. This makes it easy to retrofit a system according to the present invention to existing aircraft. It should be noted that the system may also detect chemical compounds hidden, for example, in luggage or underneath the clothing of a passenger. Even if these compounds are well hidden, minimal amounts of the chemical substance can nevertheless be found in the cabin air. Due to the capability of the sensors to detect very low concentrations of chemical compounds in the air, these minimal amounts can be detected by the sensors used in the system according to the present invention.

In a preferred embodiment each sensor of the plurality of sensors is adapted to determine a presence of a second chemical compound in the air of the aircraft cabin and to transmit data indicative of the determined presence to the processing unit. The processing unit is adapted to process data indicative of the presence of the second chemical compound received from a sensor of the plurality of sensors and to signal a user via the user interface if data indicative of the presence of the first chemical compound and data indicative of the presence of the second chemical compound have been processed by the processing unit.

According to the preferred embodiment the sensor is adapted to determine the presence of multiple chemical compounds in the air and, in particular, of a specific second chemical compound. The sensor could, for example, perform a spectral analysis to determine if a second chemical compound or substance in particulate or gaseous form is present in a low concentration in the air of the aircraft cabin. The exemplary embodiments described with regard to determining the presence of the first chemical compound and transmitting data indicative of the presence of the first chemical compound also apply to the second chemical compound. Further, the data indicating the presence of the second chemical compound may also be processed by the processing unit in a corresponding manner as the data for the first chemical compound. However, it is also possible that the data relating to the presence of the second chemical compound is processed differently.

If the processing unit determines that data indicative of the presence of both the first and the second chemical substance have been processed, a user is signaled via the user interface. For example, a notice may be displayed on an LCD display informing a user that the first and the second chemical compound have been detected by the sensors of the system. In an exemplary embodiment, the first and the second chemical substances may be harmless by themselves but if combined form an explosive. Determining that both chemical compounds have been processed by the processing system may be subject to further restrictions. For example, the system may only notify the user if data indicating the presence of both compounds is signaled during the same flight.

Thus, in the preferred embodiment the system is advantageously able to detect if two components that could be used to form an explosive are brought separately onboard an aircraft where they could be combined by a passenger of doubtful intentions.

In a preferred embodiment the system is adapted to not signal a user via the user interface if only data indicative of the presence of the first or the second chemical compound have been processed by the processing unit. This may be particularly advantageous if the two chemical compounds by themselves are harmless and, for example, common goods that are frequently transported by passengers in their carry-on luggage.

While the previous embodiments have only been described with respect to two chemical compounds, the system may in the same manner be extended to three or more chemical compounds. In this case the sensors would need to be adapted to determine a presence of each of the chemical compounds, transmit corresponding data to the processing unit where the data indicating the presence of each of the compounds would be evaluated. If data indicating the presence of a previously defined set of chemical compounds is processed by the processing unit, the processing unit may signal a user via the user interface that the predefined set off chemical compounds has been detected in the air of the aircraft cabin.

In a preferred embodiment the system comprises at least two sensors. The processing unit is adapted to signal a user via the user interface if data indicative of the presence of the first chemical compound has been transmitted by one of the sensors and data indicative of the presence of the second chemical compound has been transmitted by another one of the sensors.

In other words, the system comprises at least two sensors which are arranged in different locations. If one the sensors detects the presence of the first chemical compounds and another one of the sensors detects another one of the chemical compounds and both sensors transmit corresponding data to the processing unit, the processing unit determines that both substances are onboard an aircraft and, therefore, signals this to a user via the user interface, i.e., a warning is issued to a user. Thereby, advantageously it can be detected if chemical compounds that potentially form an explosive are carried onboard an aircraft by different persons, for example, through different doors.

Once again, while the previous embodiment has been described with regard to two chemical compounds, it can be readily extended to three or more chemical compounds detected by two or more different sensors of the system.

It is further preferred that each sensor of the plurality of sensors is adapted to determine a quantity of the first and/or the second chemical compound in the air of the aircraft cabin and to transmit data indicative of the determined quantity to the processing unit. The processing unit is adapted to process data indicative of the quantity of the first chemical compound and/or the second chemical compound received from a sensor of the plurality of sensors and to signal a user via the user interface only if the determined quantity exceeds a threshold.

In other words, the sensors according to the preferred embodiment not only transmit data corresponding to the presence of the chemical compound in the air but also quantify the amount of the substance that was detected, for example, by transmitting a measure for the concentration of the detected chemical compound in the cabin air. The processing unit evaluates the transmitted quantities and compares them to thresholds stored, for example, in a memory attached to the processing unit and only signals the user if the detected quantity exceeds a predetermined threshold.

Thereby it is possible to prevent signaling of a user if concentrations are detected in the air of the aircraft cabin that are too low as that they could indicate a sufficient amount of one of the chemical compounds to pose a potential thread. For example, if there should be a noise on a sensor with regard to a specific chemical compound, this noise could be considered to avoid false positive alarms.

It is further preferred if the processing unit is adapted to signal a user via the user interface only if the determined quantity of the first chemical compound exceeds a first threshold and the determined quantity of the second chemical compound exceeds a second threshold. Hence, the preferred embodiment ensures that the user is only signaled if both chemical compounds are present in a sufficiently high manner.

In an exemplary preferred embodiment the processing unit comprises a memory with a software for processing data from the first and/or second chemical compound. The software may be updateable such that data relating to different first and/or second chemical compounds may be processed by the processing unit at different times. For example, upon installation the processing unit may only be able to process data relating to a first and a second chemical compound. After some time the software may be updated such that the software may now also be able to process data relating to the presence and/or quantity of a third and/or a fourth chemical compound. Preferably, the sensors are broadband sensors which can detect a presence and/or quantity of a plurality of chemical compounds. Additionally or alternatively, the sensors are preferably controlled by integrated circuits which have an updatable firmware such that the sensors can be provided with a firmware update to determine a presence and/or quantity of a third and/or a fourth chemical compound. These preferred exemplary embodiments have the advantage that the system can be adjusted if different chemical compounds are used as threats.

In a second aspect the problem is solved by an aircraft cabin comprising a system for detecting low concentrations of specific chemical compounds in the air of the aircraft cabin according to any of the preceding embodiments. The aircraft cabin comprises a plurality of doors, wherein adjacent to each door at least one of the sensors of the system is arranged, and/or at least one overhead compartment, wherein at least one of the sensors of the system is arranged inside and/or underneath the at least one overhead compartment, and/or at least one passenger service unit, wherein at least one of the sensors of the system is part of the at least one passenger service unit.

The aircraft cabin according to the present invention shares the advantages of the particular embodiment of the system used therein. The aircraft cabin may comprise a plurality of elements and it is particularly advantageous to locate sensors of the system adjacent to the elements. For example, it is particularly advantageous to locate sensors adjacent to the doors of the aircraft cabin, for example, in the doorframe, to detect if the first and/or the second chemical compound are carried onboard the aircraft.

If the chemical compounds are carried inside the aircraft cabin in a luggage item which is stored in an overhead compartment, it would be particularly useful if one or more sensors were arranged in the overhead compartments. The luggage item will be stored for a considerable amount of time in the overhead compartment before it is taken out for the first time. This increases the probability of detecting the first and/or the second chemical compound in the air of the aircraft cabin.

Further, it may be advantageous to arrange sensors in the PSUs directly overhead the passengers. If a passengers carries the first and/or the second chemical compound in his clothing or directly on his body, the chances of detecting the compounds considerably increases as the passenger sits right underneath a PSU for a considerably amount of time.

In an exemplary preferred embodiment the sensors are installed in ducts of the air conditioning system which ducts are used to remove air from the aircraft cabin. As air is actively ingested into these ducts and there is a constant flow past the sensors, the chances of detecting a compound are particularly high. Further, in another exemplary embodiment at least some of the sensors are installed in the lavatories of the aircraft cabin. This may be particularly useful if an explosive shall be detected that is mixed from one or more chemical compounds inside the aircraft cabin.

Evidently, the sensors can be installed in one or more and also other locations than those described above.

In a preferred embodiment the processing unit of the system is adapted to signal a user via the user interface if data indicative of the presence of the first chemical compound has been transmitted by a sensor located in a first location in the aircraft cabin and data indicative of the presence of the second chemical compound has been transmitted by a sensor located in a second location in the aircraft cabin, wherein the first location is spaced apart from the second location. Hence, advantageously it can be detected if the first and the second chemical compound are carried onboard the aircraft by different persons or stored in different locations.

The first location is preferably located adjacent to a first door of the aircraft cabin and the second location is preferably located adjacent to a second door of the aircraft cabin or the first location is preferably located inside a first overhead compartment and the second location is preferably located inside a second overhead compartment or the first location is preferably a first passenger supply unit and the second location is preferably a second passenger supply unit. It is, for example, also possible to combine different of the above first and second locations.

According to an exemplary aspect the object underlying the present invention is also solved by an aircraft comprising an aircraft cabin according to one of the previously described embodiments. The advantages of the aircraft correspond to the advantages of the aircraft cabin comprised therein.

In another aspect the object underlying the present invention is solved by a method for detecting low concentrations of specific chemical compounds in the air of an aircraft cabin, the method comprising the steps of determining a presence of a first chemical compound in the air of an aircraft cabin, transmitting data indicative of the determined presence to a processing unit of a cabin management system, processing data indicative of the presence of the first chemical compound with the processing unit and signaling to a user via a user interface that data indicative of the presence of the first chemical compound has been processed by the processing unit.

The method preferably additionally comprises the steps of determining a presence of a second chemical compound in the air of the aircraft cabin, transmitting data indicative of the determined presence to the processing unit, processing data indicative of the presence of the second chemical compound with the processing unit and signaling a user via the user interface if data indicative of the presence of the first chemical compound and data indicative of the presence of the second chemical compound have been processed by the processing unit.

It is further preferred that no user is signaled if only data indicative of the presence of the first or the second chemical compound have been processed by the processing unit.

Preferably, the presence of the first chemical compound is determined in a first location in the air of the aircraft cabin and wherein the presence of the second chemical compound is determined in a second location in the air of the aircraft cabin.

In another preferred embodiment of the method determining the presence of the first and/or the second chemical compound includes determining a quantity of the first and/or the second chemical compound in the air of the aircraft cabin, transmitting data indicative of the presence to the processing unit includes transmitting data indicative of the determined quantity to the processing unit, processing the data indicative of the presence of the first chemical compound and/or the second chemical compound with the processing unit includes processing the data indicative of the quantity of the first chemical compound and/or the second chemical compound and a user is only signaled via the user interface if the determined quantity exceeds a threshold.

Furthermore, it is preferred that a user is only signaled via the user interface if the determined quantity of the first chemical compound exceeds a first threshold and the determined quantity of the second chemical compound exceeds a second threshold.

The aspects and advantages described above with regard to the respective embodiments of a system and an aircraft cabin according to the present invention also apply to those embodiments of the method according to the present invention that comprise corresponding features.

SUMMARY OF THE DRAWINGS

In the following the present invention will be described in more detail with regard to exemplary embodiments of the present invention shown in the Figures, wherein.

DETAILED DESCRIPTION OF THE INVENTION

Figure 1:
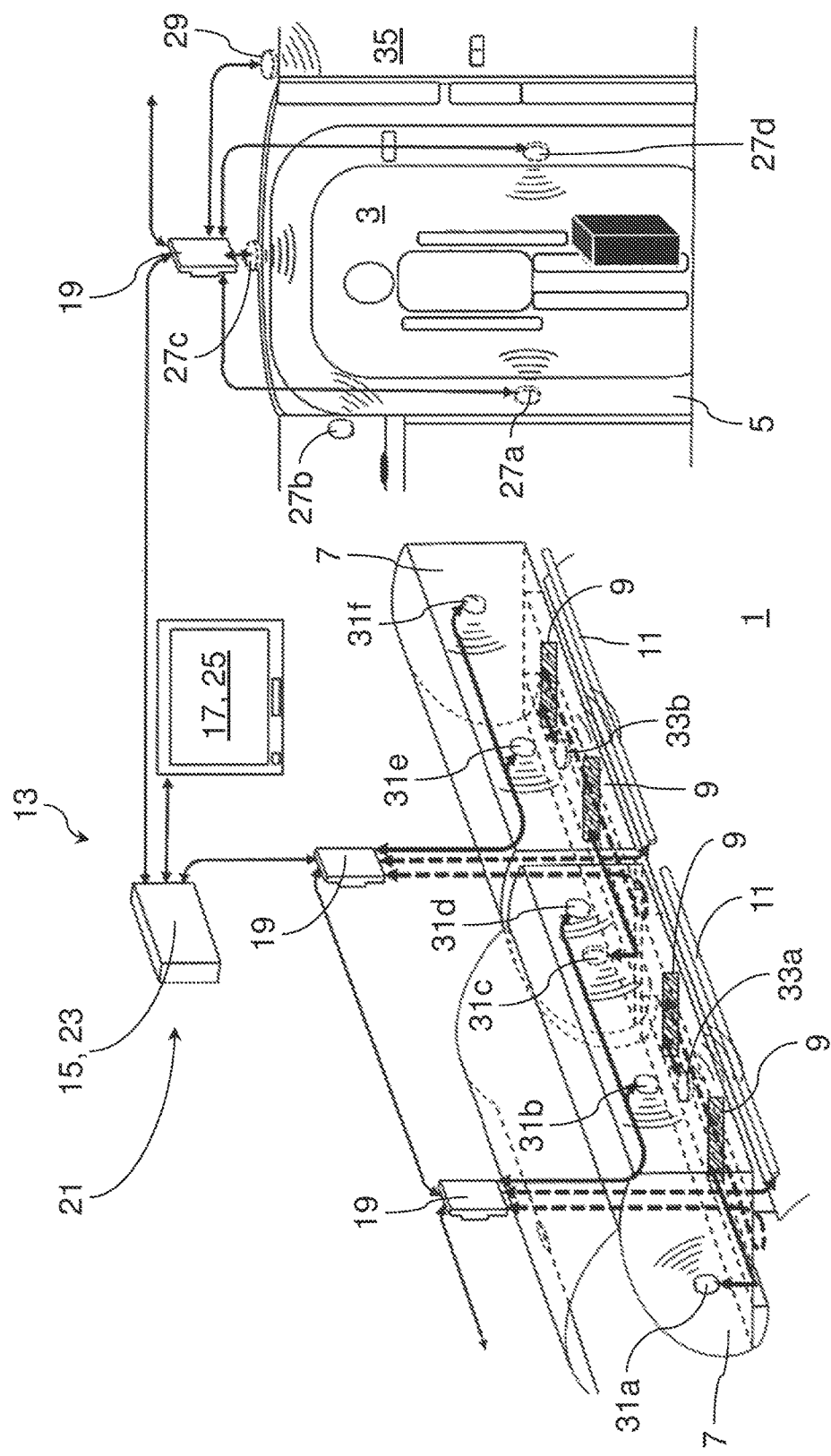
FIG. 1 shows a schematic drawing of an exemplary embodiment of an aircraft cabin according to the present invention comprising an exemplary embodiment of a system according to the present invention.

FIG. 1 shows an exemplary embodiment of an aircraft cabin 1 according to the present invention. Only a small part of the aircraft cabin 1 is shown in FIG. 1. It is pointed out that FIG. 1 is a schematic drawing illustrating those elements of the aircraft cabin 1 only that are relevant in the context of the present invention. The elements shown in FIG. 1 are not shown to scale and are in particular not necessarily shown in the correct relative and absolute positions with regard to one another.

The aircraft cabin 1 comprises a door 3 surrounded by a door frame 5 and a plurality overhead compartments 7. Only two of the overhead compartments 7 are shown in FIG. 1. The overhead compartments 7 are arranged above the passenger seats (not shown) in the cabin. They provide space for storing carry-on luggage items and are also used for mounting passenger service units (PSUs) 9 and cabin lighting 11.

The aircraft cabin 1 further comprises a cabin management system 13 which at least comprises a central processing unit 15 and a user interface 17. In the present embodiment the user interface 17 is a touchscreen display also referred to as flight attendant panel 17. The flight attendant panel 17 is used for controlling various features of the cabin 1. For example, the cabin lighting 11 and the PSUs 9 are connected to and controlled by the cabin management system 13.

In the embodiment shown in FIG. 1, an Ethernet network is provided in the aircraft cabin 1. The Ethernet network comprises a plurality of data distribution devices 19 which are connected to the central processing unit 15 via the network. The connection may, for example, be provided by wired data lines as shown in FIG. 1. However, it is also be possible to provide a wireless connection between the central processing unit 15 and the data distribution devices 19. The data distribution devices 19 are arranged in between the central processing unit 15 and other elements of the cabin 1 controlled by the cabin management system 13. For example, the PSUs 9 and the cabin lighting 11 are connected to the central processing unit 15 of the cabin management system 13 via the data distribution elements 19. The data distribution elements 19 are primarily used to transmit data between different elements in the aircraft cabin 1. However, they may also supply power to some of the elements, such as the cabin lighting 11. Data can be transmitted via the network of the cabin management system 13 in both directions i.e., from the PSUs 9 to the central processing unit 15 and in the opposite direction.

The cabin management system 13 is also part of an exemplary embodiment of a system 21 for detecting low concentrations of specific chemical compounds in the air of the aircraft cabin 1. The central processing unit 15 of the cabin management system 13 forms a processing unit 23 of the system 21. Likewise, the user interface 17 forms a user interface 25 of the system 21.

Additionally the system comprises a plurality of sensors 27a to 27d, 29, 31a to 31f, 33a, 33b. Each of the sensors 27a to 27d, 29, 31a to 31f, 33a, 33b is connected to the processing unit 23 such that data can be transmitted from the sensors 27a to 27d, 29, 31a to 31f, 33a, 33b to the processing unit 23 and in the opposite direction. Further, each of the sensors 27a to 27d, 29, 31a to 31f, 33a, 33b is adapted to determine a presence and a quantity of a first and a second chemical compound in the air of the aircraft cabin 1. Data indicating that the presence of the first and/or the second chemical compound has been detected in the air of the aircraft cabin 1 can be transmitted from the sensors 27a to 27d, 29, 31a to 31f, 33a, 33b to the processing unit 23 via the Ethernet network. Further, also data indicating the quantity of the first and/or the second chemical compound detected in the air of the aircraft cabin can be transmitted from the sensors 27a to 27d, 29, 31a to 31f, 33a, 33b to the processing unit 23.

The sensors 27a to 27d, 29, 31a to 31f, 33a, 33b are preferably controlled or operated by integrated circuits (not shown) comprising a firmware. This firmware can be updated such that the sensors 27a to 27d, 29, 31a to 31f, 33a, 33b can be adapted to detect different chemical compounds at different points in time. For example, the sensors 27a to 27d, 29, 31a to 31f, 33a, 33b may be adapted to determine a presence and a quantity of a first and a second chemical compound when they are installed. After some time the firmware on the integrated circuits is updated and the sensors 27a to 27d, 29, 31a to 31f, 33a, 33b may now also determine a presence of a third and a fourth chemical compound.

The processing unit 23 is adapted to process received data indicating the presence and the quantity of the first and the second chemical compound in the air of the aircraft cabin 1. If data indicating that the first chemical compound is present in the air of the aircraft cabin 1 has been transmitted to the processing unit 23, the latter signals a user via the user interface 25 accordingly. For example, the processing unit 23 may instruct the user interface 25 to display a message indicating that a first chemical compound has been detected in the air of the aircraft cabin 1. Thereby, it is advantageously possible to signal, for example, the cabin personal if a passenger of an aircraft brings on board prohibited chemical substances such as a prohibited first chemical compound.

It is also possible that the processing unit 23 first evaluates the quantity of the first chemical compound in the air of the aircraft cabin 1 and only signals a user via the user interface 25 if the quantity exceeds a predetermined threshold. Thereby, it is ensured that a user is only signaled if a significant amount of the first chemical compound was detected in the air of the aircraft cabin 1.

In an exemplary embodiment a software is provided on a memory (not shown) of the processing unit 23. This software is used for processing data indicating the presence and/or quantity of the first and/or second chemical compounds transmitted by the sensors 27a to 27d, 29, 31a to 31f, 33a, 33b. The software is updateable, for example, by updating a data base that is part of the software, such that the software may be adapted to process different first and/or second chemical compounds at different points in time or to process a first and/or second chemical compound when installed and additionally process a third and a fourth chemical compound at a later point in time. In a preferred exemplary embodiment the sensors 27a to 27d, 29, 31a to 31f, 33a, 33b are broadband sensors 27a to 27d, 29, 31a to 31f, 33a, 33b which transmit a broad spectrum to the processing unit 23. As the spectrum is analyzed by the processing unit 23, it is sufficient to update the processing unit 23 for detecting additional chemical compounds.

Further, the system 21 may be adapted such that a user is only signaled if data indicating the presence of both the first and the second chemical compound has been detected by sensors 27a to 27d, 29, 31a to 31f, 33a, 33b of the system 21. In addition, it may be necessary that for each of the first and the second chemical compound a different threshold has been defined and a user is only signaled via the user interface 25 if both thresholds are exceeded by the quantity of the first and the second chemical compound detected in the air of the aircraft cabin 1. This has the advantage that it is impossible to find chemical substances on board an aircraft that need to be combined to form a hazardous chemical such as an explosive.

The processing unit 23 is in particular adapted to signal a user via the user interface 25 of the presence of the first and the second chemical compound if their presence and/or a significant quantity of the compounds in the air of the aircraft cabin 1 has been picked up by different sensors 27a to 27d, 29, 31a to 31f, 33a, 33b of the system 21, i.e., by a sensor located in a first location and another sensor located in a second location. This has the advantage that it can be detected if one of the chemical compounds is stored in a different location than the other one or if chemical compounds are transported inside the aircraft cabin 1 by different passengers, for example, through different cabin doors 3.

The aircraft cabin 1 shows a plurality of preferred locations for locating the sensors 27a to 27d, 29, 31a to 31f, 33a, 33b of the exemplary embodiment of the system 21. The locations pointed out below are preferred first and second locations for locating sensors 27a to 27d, 29, 31a to 31f, 33a, 33b and detecting first and second chemical compounds in the air of the aircraft cabin 1. For example, four sensors 27a to 27d are arranged in the frame 5 of a cabin door 3. The sensors 27a to 27d are provided for detecting chemical compounds carried on board the aircraft, i.e. inside the aircraft cabin 1, by a passenger. Another sensor 29 is arranged inside a lavatory 35 to detect if a passenger intends to combine two chemical compounds to form a third chemical compound which could be used as an explosive. Further sensors 31a to 31f are arranged inside the overhead compartments 7 where they can advantageously detect chemical compounds hidden in the carry-on luggage of passengers. Finally, sensors 33a, 33b are part of PSUs 9 arranged underneath the overhead compartments 7 and right above the passenger seats. Here, they can advantageously detect first and the second chemical compounds carried by passengers on their body. All of these embodiments have the advantage that they are particularly useful to detect hidden chemical compounds which only evaporate at very low rates and with very low concentrations into the air of the aircraft cabin 1.

The exemplary embodiments of a system 21 and an aircraft cabin 1 according to the present invention have been described with reference to two chemical substances only. However, the system 21 and the aircraft cabin 1 can readily be extended for detecting a plurality of different chemical compounds.

Figure 2:
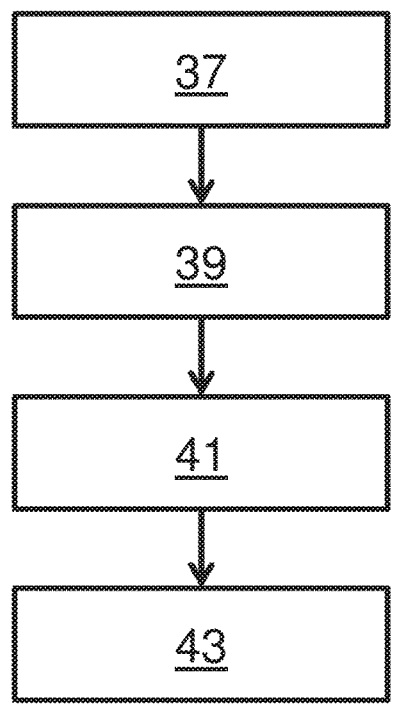
FIG. 2 shows a flow chart of a first exemplary embodiment of a method according to the present invention and FIG. 3 shows a flow chart of a second exemplary embodiment of a method according to the present invention.

FIG. 2 shows a first exemplary embodiment of a method according to the present invention. The method can, for example, be carried out inside the aircraft cabin 1 using the system 21 for detecting low concentrations of specific chemical compounds in the air of the aircraft cabin 1.

In a first step 37 presence of a first chemical compound is detected in the air of the aircraft cabin 1. Detecting a presence of the first chemical compound includes detecting a quantity of the first chemical compound in the air of the aircraft cabin 1, for example, detecting a concentration of the first chemical compound. To this end, one of the sensors 27a to 27d, 29, 31a to 31f, 33a, 33b may be used. In a second step 39 data indicating the presence of the first chemical compound and the quantity of the first chemical compound in the air of the aircraft cabin 1 are transmitted to the processing unit 25 where the data is processed in a third step 41. Finally, in a fourth step 43 a user is signaled via the user interface 25 if the first chemical compound has been detected in a quantity exceeding a predetermined threshold.

The advantages of the first exemplary embodiment of a method according to the present invention correspond to the advantages of the respective system 21 used to carry out the steps 37, 39, 41, 43 of the method.

Figure 3:
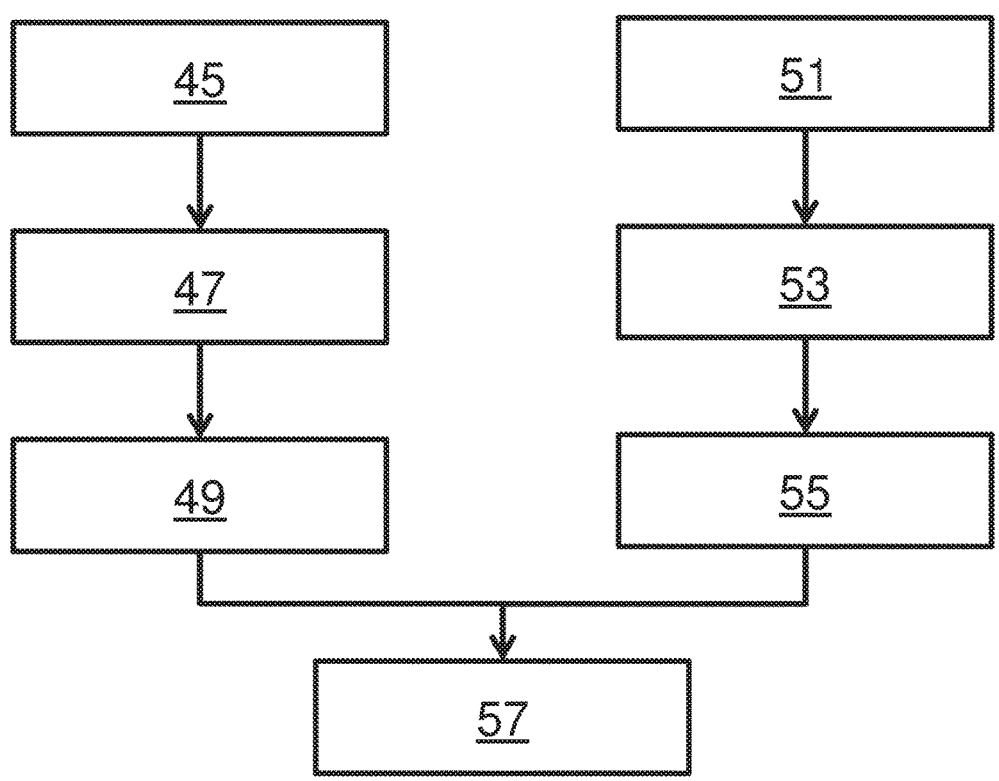

A second exemplary embodiment of a method according to the present invention also preferably employing the system 21 and the aircraft cabin 1 is shown in FIG. 3. Here, in a first step 45 the presence and the quantity of a first chemical compound in the air of the aircraft cabin 1 is detected using a sensor 27a to 27d, 29, 31a to 31f, 33a, 33b located in a first location. In a second step 47 data indicating the presence and the quantity of the first chemical compound is transmitted to the processing unit 23 where it is processed in a third step 49.

In a fourth step 51 the presence and the quantity of a second chemical compound in the air of the aircraft cabin 1 are detected using a sensor 27a to 27d, 29, 31a to 31f, 33a, 33b located in a second location. In a fifth step 53 data indicating the presence and the quantity of the second chemical compound is transmitted to the processing unit 23 where it is processed in a sixth step 55. The first to third step 45, 47, 49 and the fourth to sixth step 51, 53, 55 may be executed in parallel as shown in FIG. 3 or in sequential order. Alternatively, the first to third step 45, 47, 49 may be executed before or after the fourth to sixth step 51, 53, 55. However, there may be a limited time span in which the first to third step 45, 47, 49 and the fourth to sixth step 51, 53, 55 have to be executed. The time span may, for example, be limited to the duration of a single flight, wherein a flight begins when the first passenger boards the aircraft cabin 1 and ends when the last passenger has exited the aircraft cabin 1.

In a final step 57 a user is signaled via the user interface 25 that the first and the second chemical compound has been detected in the air of the aircraft cabin 1 if the quantities detected by the sensors 27a to 27d, 29, 31a to 31f, 33a, 33b in the first and the second location exceed predetermined thresholds for both chemical compounds. Thereby, the method advantageously provides a means to detect an explosive that is manufactured from two chemical compounds that are by themselves harmless. Furthermore, as both chemical compounds have to be detected before a user is signaled, false alarms if only one of the compounds which is harmless by itself is brought on board an aircraft are prevented.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A system for detecting low concentrations of specific chemical compounds in the air of an aircraft cabin, the system comprising:
   a cabin management system, and a plurality of sensors,
   wherein the cabin management system comprises a processing unit and a user interface, and
   wherein each sensor of the plurality of sensors is connected to the processing unit of the cabin management system such that data is to be transmitted from the sensor to the processing unit,
   wherein the plurality of sensors are adapted to:
      determine a presence of a first chemical compound in the air of an aircraft cabin and transmit data indicative of the determined presence of the first chemical compound to the processing unit, and
      determine a presence of a second chemical compound in the air of the aircraft cabin and to transmit data indicative of the determined presence of the second chemical compound to the processing unit;
   wherein the processing unit is adapted to:
      process the data indicative of the presence of the first chemical compound received from the plurality of sensors;
   process the data indicative of the presence of the second chemical compound received from the plurality of sensors;
   signal a user via the user interface if the data indicative of the presence of the first chemical compound and the data indicative of the presence of the second chemical compound have been processed by the processing unit, and
   not signal a user via the user interface if the procession unit does not process either of data indicative of the presence of the first or data indicative of the second chemical compound.

2. The system according to claim 1, wherein the system comprises at least two sensors, and
   wherein the processing unit is adapted to signal a user via the user interface if the data indicative of the presence of the first chemical compound has been transmitted by one of the plurality of sensors and the data indicative of the presence of the second chemical compound has been transmitted by another one of the plurality of sensors.

3. The system according to claim 1, wherein each sensor of the plurality of sensors is adapted to determine at least one of a quantity of the first chemical compound and the second chemical compound in the air of the aircraft cabin, and to transmit data indicative of the determined quantity to the processing unit, and
wherein the processing unit is adapted to process data indicative of the quantity of at least one of the first chemical compound and the second chemical compound received from a sensor of the plurality of sensors, and to signal a user via the user interface only if the determined quantity exceeds a threshold.

4. The system according to claim 3, wherein the processing unit is adapted to signal a user via the user interface only if the determined quantity of the first chemical compound exceeds a first threshold and the determined quantity of the second chemical compound exceeds a second threshold.

5. An aircraft cabin comprising:
a system for detecting low concentrations of specific chemical compounds in the air of the aircraft cabin, wherein the system comprises:
a cabin management system including:
a plurality of sensors each adapted to determine a presence of a first chemical compound in the air of the aircraft cabin and transmit data indicative of the determined presence of the first chemical compound;
a processing unit configured to receive and process the data indicative of the presence of the first chemical compound, and to signal a user via a user interface if the data indicative of the presence of the first chemical compound has been processed by the processing unit;
wherein the aircraft cabin further comprises at least one of:
a plurality of doors, wherein adjacent to each door of the plurality of doors is at least one of the plurality of sensors;
at least one overhead compartment, wherein at least one of the plurality of sensors is arranged inside the at least one overhead compartment, and
at least one passenger service unit, wherein at least one of the plurality of sensors is part of the at least one passenger service unit.

6. The aircraft cabin according to claim 5, wherein the processing unit of the system is adapted to signal a user via the user interface if the data indicative of the presence of the first chemical compound has been transmitted by at least one of the plurality of sensors located in a first location in the aircraft cabin and data indicative of the presence of a second chemical compound has been transmitted by another one of the plurality of sensors located in a second location in the aircraft cabin,
wherein the first location is spaced apart from the second location.

7. The aircraft according to claim 6, wherein the first location is located adjacent to a first door of the plurality of doors of the aircraft cabin and the second location is located adjacent to a second door of the plurality of doors of the aircraft cabin, or wherein, the at least one overhead compartment includes a first overhead compartment and a second overhead compartment, and the first location is located inside the first overhead compartment and the second location is located inside the second overhead compartment or
wherein, the at least one passenger service unit includes a first passenger service unit and a second passenger service unit, and the first location is at the first passenger supply unit and the second location is at the second passenger supply unit.

8. A method for detecting low concentrations of specific chemical compounds in the air of an aircraft cabin, the method comprising the steps of:
determining a presence of a first chemical compound in the air of an aircraft cabin,
transmitting data indicative of the determined presence of the first chemical compound to a processing unit of a cabin management system,
determining a presence of a second chemical compound in the air of the aircraft cabin, wherein the presence of the first chemical compound is determined at a first location in the air of the aircraft cabin and the presence of the second chemical compound is determined at a second location in the air of the aircraft cabin;
transmitting data indicative of the determined presence of the second chemical compound to the processing unit
processing, by the processing unit, the data indicative of the presence of the first chemical compound and the data indicative of the presence of the second chemical compound; and
signaling a user via a user interface if the processing unit processes both the data indicative of the presence of the first chemical compound and the data indicative of the presence of the second chemical compound.

9. The method according to claim 8, wherein no user is signaled if the processing unit does not process either data indicative of the presence of the first or data indicative of the second chemical compound.

10. The method according to claim 8, wherein the determining the presence of the first chemical compound and the second chemical compound includes determining a quantity of at least one of the first chemical compound in the air in the aircraft cabin and a quantity of the second chemical compound in the air of the aircraft cabin,
wherein the transmission of the data indicative of the presence to the processing unit includes transmitting data indicative of the determined quantity to the processing unit,
wherein the processing of the data with the processing unit includes processing the data indicative of the quantity of at least one of the first chemical compound and the second chemical compound, and
wherein a user is only signaled via the user interface if the determined quantity exceeds a threshold.

11. The method according to claim 10, wherein a user is only signaled via the user interface if the determined quantity of the first chemical compound exceeds a first threshold and the determined quantity of the second chemical compound exceeds a second threshold.

* * * * *